(12) United States Patent
Hamadallah

(10) Patent No.: US 8,766,765 B2
(45) Date of Patent: Jul. 1, 2014

(54) DEVICE, METHOD AND COMPUTER PROGRAM PRODUCT TO ASSIST VISUALLY IMPAIRED PEOPLE IN SENSING VOICE DIRECTION

(76) Inventor: Hassan Wael Hamadallah, Newark, DE (US)

( * ) Notice: Subject to any disclaimer, the term of this patent is extended or adjusted under 35 U.S.C. 154(b) by 153 days.

(21) Appl. No.: 13/618,723

(22) Filed: Sep. 14, 2012

(65) Prior Publication Data

US 2014/0077925 A1 Mar. 20, 2014

(51) Int. Cl.
*G09B 21/00* (2006.01)

(52) U.S. Cl.
USPC .... 340/4.12; 381/313; 381/327; 704/E21.019

(58) Field of Classification Search
CPC ...................................................... G10L 21/06
See application file for complete search history.

(56) References Cited

U.S. PATENT DOCUMENTS

| | | | | |
|---|---|---|---|---|
| 5,029,216 A * | 7/1991 | Jhabvala et al. | | 381/313 |
| 7,648,326 B2 * | 1/2010 | Santele et al. | | 414/723 |
| 8,543,061 B2 * | 9/2013 | Suhami | | 455/41.3 |
| 2001/0016818 A1 * | 8/2001 | Hara et al. | | 704/500 |
| 2005/0046789 A1 * | 3/2005 | Jannard et al. | | 351/158 |
| 2006/0003803 A1 * | 1/2006 | Thomas et al. | | 455/556.1 |
| 2007/0160254 A1 * | 7/2007 | Ritter et al. | | 381/381 |
| 2008/0151179 A1 * | 6/2008 | Howell et al. | | 351/158 |
| 2010/0110368 A1 * | 5/2010 | Chaum | | 351/158 |

FOREIGN PATENT DOCUMENTS

| | | |
|---|---|---|
| EP | 1 538 874 | 3/2011 |
| JP | 3948066 | 4/2007 |
| JP | 2010-79182 | 4/2010 |
| KR | 10-2010-004642 | 1/2010 |
| WO | 2012/001587 | 1/2012 |

* cited by examiner

*Primary Examiner* — Hai Phan
*Assistant Examiner* — Ojiako Nwugo
(74) *Attorney, Agent, or Firm* — Oblon, Spivak, McClelland, Maier & Neustadt, L.L.P.

(57) ABSTRACT

A device, method and computer program product that provides tactile feedback to a visually impaired person to assist the visually impaired person in maintaining eye contact with another person when speaking to the other person. The eyeglass-based tactile response device includes a frame that has sensors mounted thereto, and a track that interconnects eyepieces on the device. In one example, a motor and a wheel are coupled to the track and are driven across the track depending on the amount of feedback to be provided to the user regarding how much the user should turn his or her head.

11 Claims, 8 Drawing Sheets

| 1° | 2° | 3° | | 180° |
|---|---|---|---|---|
| X | 2X | 3X | | 180X = L |

FIG. 8

DEVICE, METHOD AND COMPUTER PROGRAM PRODUCT TO ASSIST VISUALLY IMPAIRED PEOPLE IN SENSING VOICE DIRECTION

GRANT OF NON-EXCLUSIVE RIGHT

This application was prepared with financial support from the Saudia Arabian Cultural Mission, and in consideration therefore the present inventor(s) has granted The Kingdom of Saudi Arabia a non-exclusive right to practice the present invention.

BACKGROUND

1. Field of the Disclosure

The present disclosure relates to devices, method and a computer program product regarding mechanisms and methods that assist visually impaired people to sense voice direction using tactile response.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Conventionally, visually impaired people (e.g., blind people) use various tools to assist them in navigating through their daily lives. For example, a mechanism commonly used is a long stick to tap in front of them to identify obstacles while they are walking. Also, blind people sometimes use tools that convert sensed objects into computer-generated voice by way of specially designed equipment that converts the recognition of the sensed objects into voice commands.

As recognized by the present inventor, however, when individuals speak with one another, it is expected that the individuals maintain eye contact. This often shows a sense of interest in the conversation. If one person is not looking at the other person, it can lead to an unintended consequence of the listener or speaker believing that the other person is not interested in the conversation. However, blind people do not benefit from visual clues for detecting whether the opposing individual is aligned with the eyes of the blind person.

SUMMARY

In light of the above observations made by the present inventor, a device, method and a computer program product are provided that assist a visually impaired person to align his/her head (and eyes) to the person they are speaking with. A combination of sensors and tactile response mechanisms are used to provide tactile information to the visually impaired person to assist them in knowing when their eyes are aligned with those of the person they are speaking with. Also, the mechanism optionally provides feedback information, notifying the visually impaired person as to how far off their line of sight is from the line of sight of the person they are speaking with. This assists the visually impaired person in knowing the angular amount by which they need to turn their head to maintain eye contact.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 8 depicts a table used for populating the associations between degree of alignment and the corresponding tactile distance for a particular embodiment of the device.

DETAILED DESCRIPTION OF THE EMBODIMENTS

Figure 1:
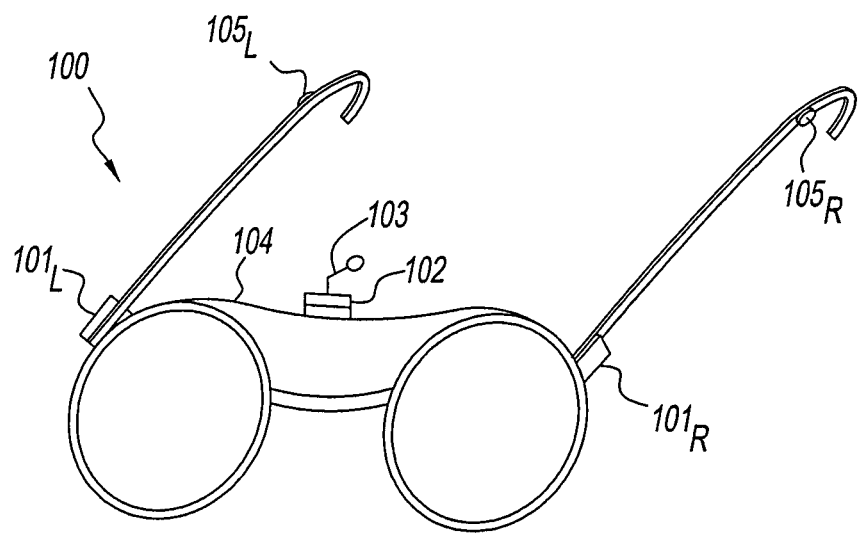
FIG. 1 is a diagram of a eyeglass-based tactile response device according to one embodiment of the disclosure.

Referring now to the drawings, like reference numerals designate identical or corresponding parts throughout the several views.

FIG. 1 is a profile view of an eyeglass-based tactile response device 100. The device 100 generally has the shape of eyeglasses that can be worn by a user. In this case, the device is intended to be worn by a person with visual impairment, perhaps even legally blind. The eyeglass-based tactile response device 100 includes left and right sensors $101_L$ and $101_R$ respectively. These sensors are shown to be placed on the temples of the eyeglasses, specifically near the hinge location of the earpiece with the eyeglass frame. The sensors need not be positioned at this specific location, but to better assist in signal processing a spacing between the sensors $101_L$ and $101_R$ is beneficial. Also, by having the sensors $101_L$ and $101_R$ at the depicted location offers the benefit of having a direct audio path to the sound source, which often is a person who is speaking with the visually impaired person.

The eyeglass-based tactile response device 100 includes a motor 102 and wheel 103 disposed on a track 104 that interconnects the eyepieces. Also, as shown in FIG. 1, the vibrators $105_L$ and $105_R$ are disposed on the earpiece of the eyeglass. The vibrators $105_L$ and $105_R$ need not be located at this particular location, but since they provide a haptic response to the user, it is desirable to have these vibrators located at a place where the eyeglass frame contacts the user's head.

As will be discussed, motor 102 and wheel 103 (a type of contact piece) are connected to one another and ride between the left and right eyepiece on the track 104. The motor 102 controllably drives the position of the wheel 103 under the direction of a controller (to be discussed). The wheel 103 is mounted on an arm and is bendable so that the wheel will contact the forehead of the user. This way, when the motor is driven either to the left or the right, the wheel 103 moves with the motor 102 and the user can sense the location of the wheel's movement since it is in contact with the user. In doing so, the user is provided with a tactile response that signals the user where to turn his/her head. For example, if the wheel 103 is driven by the motor 102 to the right side of the user's forehead, it indicates that the user should turn right. Likewise, a reciprocal response is provided if the motor 102 drives the wheel 103 to the left side of the user's forehead. When centered on the user's forehead, the user recognizes that the user is in direct line of sight with the person they are speaking to, so as to give the appearance of maintaining eye contact.

Figure 2:
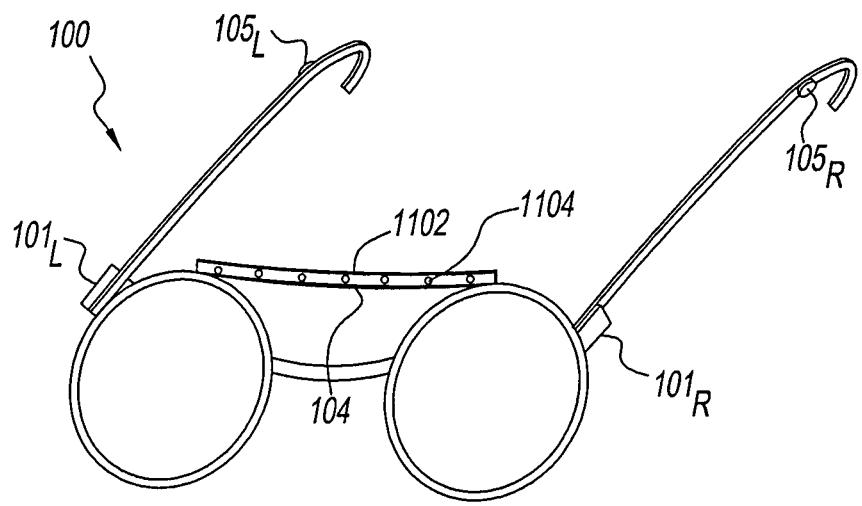
FIG. 2 shows another embodiment of the eyeglass-based tactile response device.

FIG. 2 is another embodiment of an eyeglass-based tactile response device 1000. What is different between the first embodiment and this second embodiment is that the motor 102 and wheel 103 of the device 100 is replaced with tactile protrusion bar 1102 that is formed along or in the track 104. The tactile protrusion bar 1102 includes deployable protrusion devices 1104 distributed along the track 104. The eyeglass-based tactile response device 1000 issues a tactile command to the user to turn his or her head to the left or to the right by extending one of the deployable protrusion pieces 1104 toward the forehead of the user so that the user feels a tap on the forehead, indicating that the user should turn his or her head towards the direction of the tap. This embodiment allows for relatively rapid tactile responses to be provided to the user without need to drive a mechanism across the track. It also helps to minimize overshoot.

Figure 3:
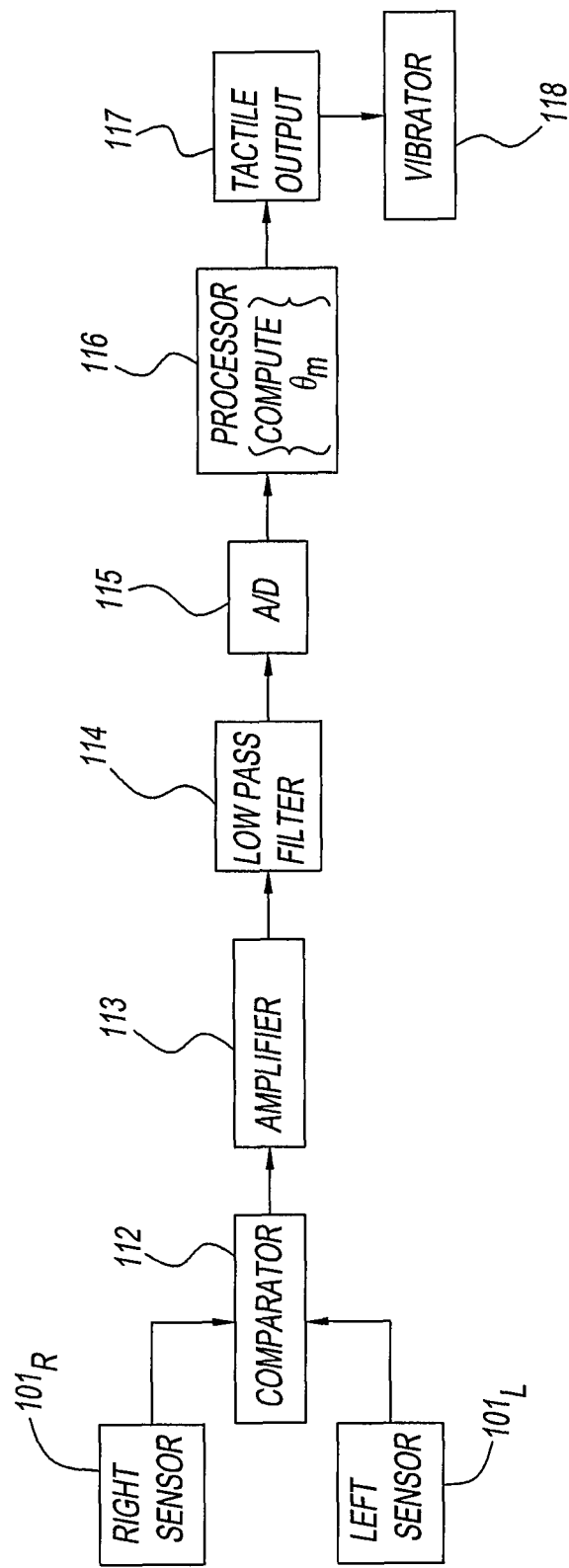
FIG. 3 is a block diagram depicting the various steps of a signal processing portion of the eyeglass-based tactile response device.

FIG. 3 is a block diagram of signal processing components employed in the eyeglass-based tactile response devices 100 (1000), which may be located in a separate module integrated into the eyeglasses frame.

The right sensor $101_R$ and the left sensor $101_L$ are microphone-based sensors that provide a transducer function, converting audio energy into an electrical signal. A comparator 112 (which may be implemented in a processor), compares the signals from the right sensor $101_R$ and left sensor $101_L$ to determine a magnitude and timing difference between the respective signals. For example, the comparator 112 may be a Texas Instrument LM311. In one embodiment, the comparator 112 compares the magnitude of the two signals so that a stronger of the two signals may be identified for downstream processing. In another embodiment, the comparator 112 provides a phase detection mechanism, where the arrival time (or phase) difference between the signals captured at the right sensor $101_R$ and at the left sensor $101_L$ is computed so that calculations may be performed to determine the orientation of the eyeglass-based tactile response device 100 (1000) to the sound source. However, the present embodiment identifies the stronger of the two signals, and the stronger signal is passed to an amplifier 113, and then the amplified signal is passed through a low pass filter 114 to remove extraneous harmonics and other interference. The amplifier 113 may be realized by using the Texas Instrument (TI) LM386, low voltage power amplifier for example. An analog to digital converter 115 (realized by a TI ADC12D800, for example) converts the output of the low pass filter into a digital signal which is then passed to the processor 116 that computes $\theta_m$, which is a bearing angle to which the user needs to turn his or her head in order to make direct eye contact i.e., aligned with the sound source. The output of the processor 116, which includes an indication of $\theta_m$ is provided to a tactile output device 117, which provides an output to drive the motor 102 (first embodiment) and the deployable protrusion pieces 1104 (second embodiment). Furthermore, when the tactile output 117 is centered on the user's forehead, or is within a user-settable acceptable range for maintaining eye contact, a signal is provided to the vibration devices $105_L$ and/or $105_R$ so as to inform the user to stop the user's motion.

Figure 4:
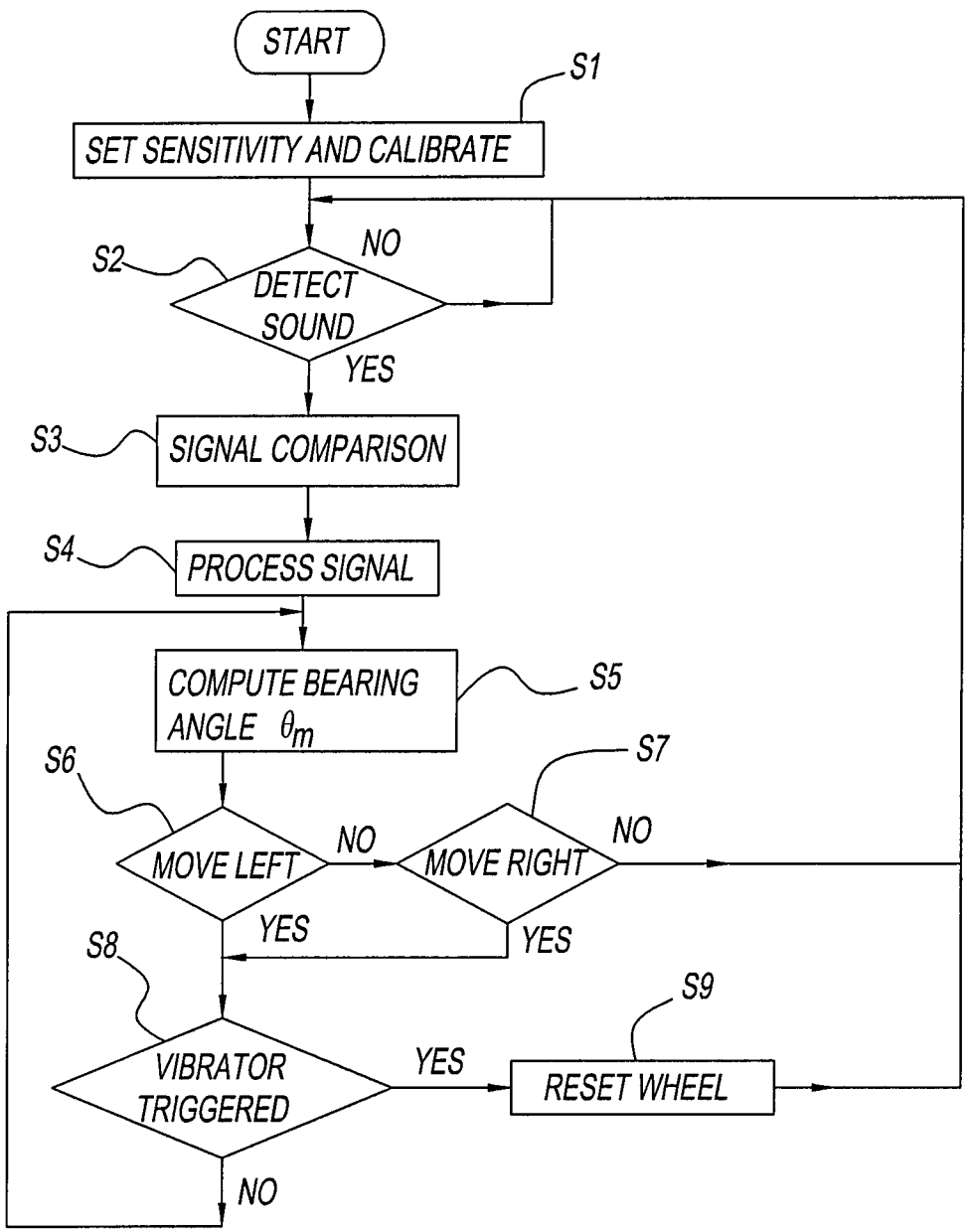
FIG. 4 is a flowchart showing a system level method used by the eyeglass-based tactile response device to provide tactile instruction to the user to assist in making eye contact with another person.

FIG. 4 is a flowchart for a process performed in the eyeglass-based tactile response device 100 (1000). The process begins at step S1 where a user may set the sensitivity and the device performs a calibration routine (described later). The process then proceeds to step S2, where a query is made regarding whether a sound is detected above a predetermined threshold. If the response to the query in step S2 is negative, the process remains in the sound detection step S2. However, if the response to the query in step S2 is affirmative, the process proceeds to step S3 where a signal comparison step is performed and a stronger of the two signals is identified (in the embodiment where one of the signals is isolated). The signal comparison may also, in an alternative environment, determine a phase angle between the two signals. The process then proceeds to step S4 where the signal is processed as discussed above with regard to FIG. 3. Once processed, a computation is made (described later) of the bearing angle ($\theta_m$) in step S5. Once $\theta_m$ is identified in step S5, the process moves to step S6 where a query is made regarding whether or not the bearing angle $\theta_m$ indicates whether the device 100 (1000) should be moved to the left. If the response is negative, the process proceeds to step S7 where another query is made regarding whether the device 100 (1000) should be moved to the right. If the response to the query in step S7 is negative, the process returns to step S2. However, if the response to the query in step S6, or the response to the query in step S7 is affirmative, the process proceeds to step S8 where a query is made regarding whether $\theta_m$ is within the acceptable range (i.e., has the vibration devices $105_L$ and $105_R$ triggered). If the response to the query in step S8 is negative, the process returns to step S5. However, if the response is affirmative, the process proceeds to step S9 where the motor 102 drives to move the wheel 103 by an incremental step. Subsequently, the process returns to step S2. In the second embodiment, instead of resetting the wheel in step S9, the appropriate deployable protrusion piece 104 is actuated to tap the user on the forehead at the appropriate location.

Figure 5:
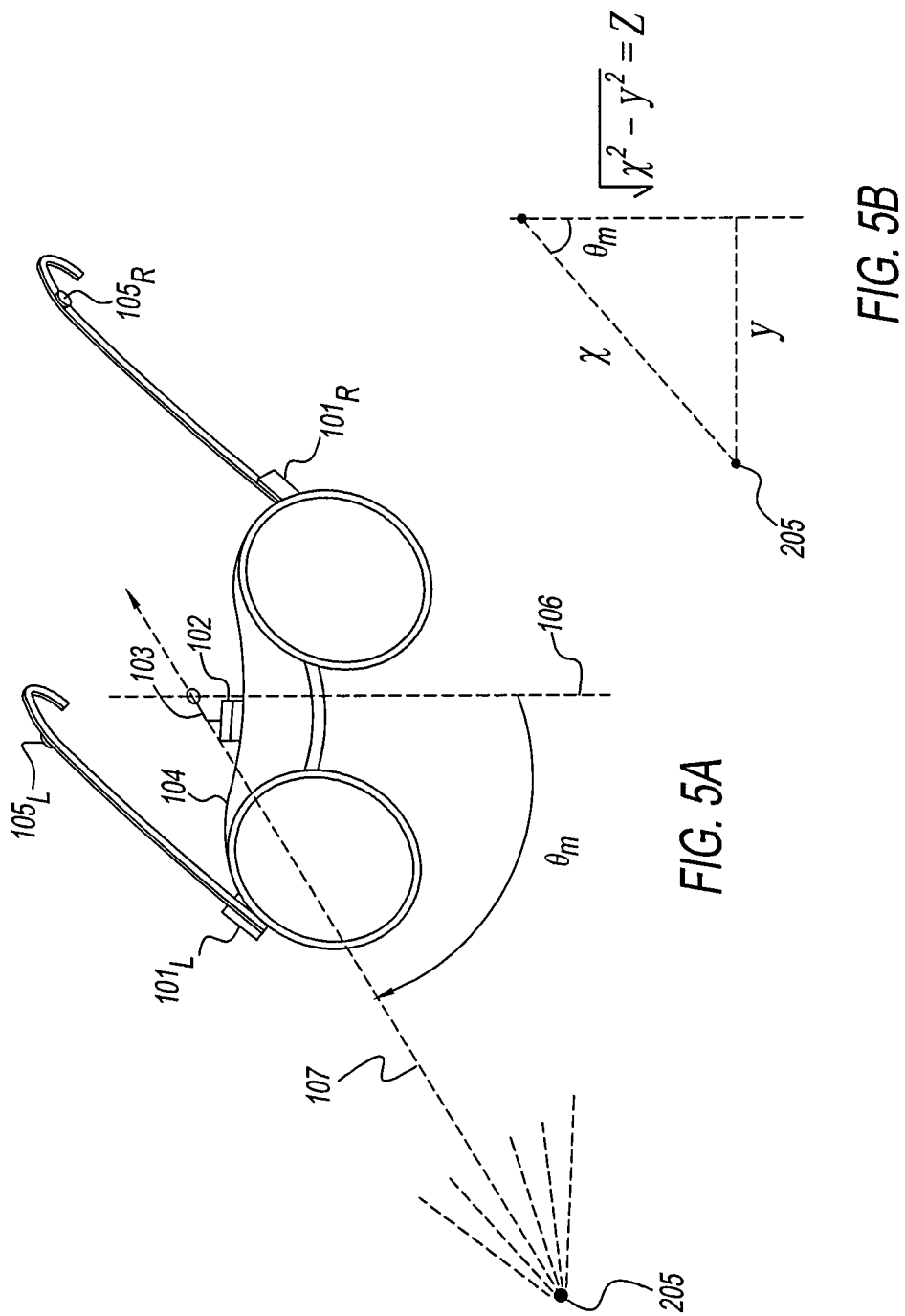
FIG. 5A is an exemplary layout of how the eyeglass-based tactile response device may be oriented relative to a sound source.
FIG. 5B depicts the bearing angle ($\theta_m$), the amount which the user is expected to turn.

FIG. 5A provides an example scenario where the eyeglass-based tactile response device 100 is offset by a bearing angle $\theta_m$, with respect to a line of voice 107, and a plane of reference 106. Moreover, as shown in FIG. 5A, the device 100 is centered on the plane of reference 106. However, the sensors $101_L$ and $101_R$ detect that the sound source 205 that is located along a line of voice 107. The device 100 then determines the bearing angle $\theta_m$, which is the angular difference between the plane of reference 106 and the line of voice 107.

Referring to FIG. 5B, it is noted that:
x is a distance of the user of the device 100 from the sound source 205.
y is a distance of the sound source from the place of reference 106.

The bearing angle $\theta_m$ can be calculated as follows:

$$\tan(\theta_m) = \frac{y}{z} \quad (1)$$

$$= \frac{y}{\sqrt{x^2 - y^2}} \quad (2)$$

$$\theta_m = \tan^{-1}\left[\frac{y}{\sqrt{x^2 - y^2}}\right] \quad (3)$$

Figure 6:
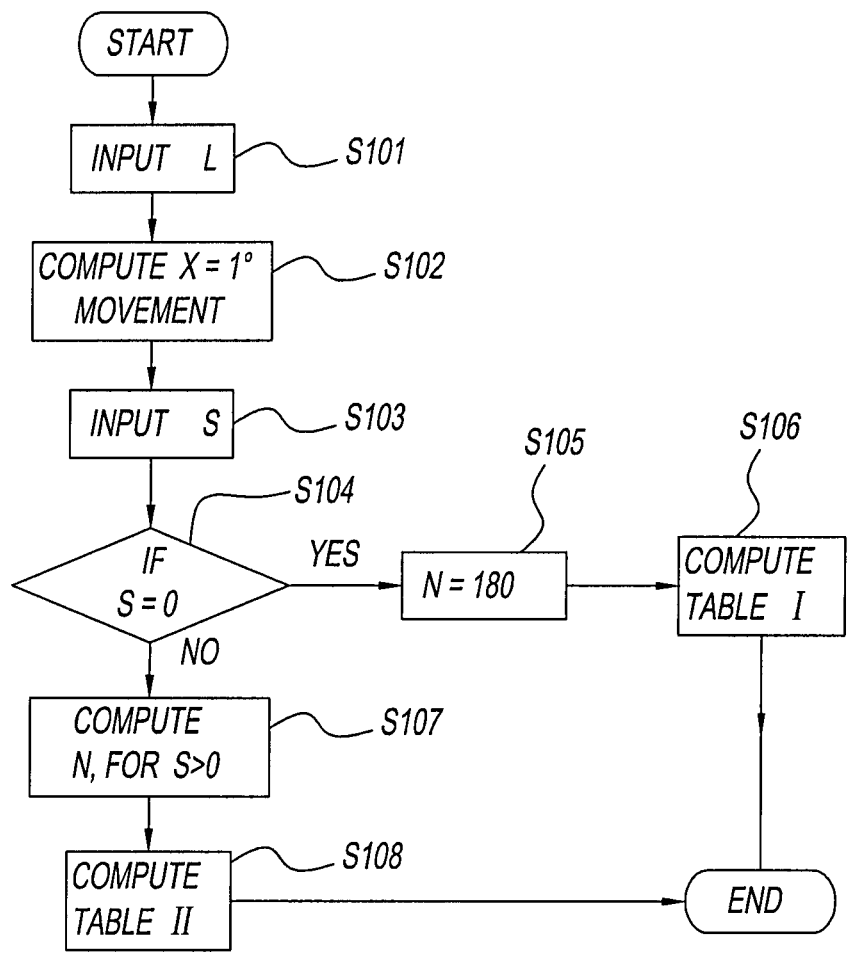
FIG. 6 is a flowchart of a process for adjusting user-defined sensitivity of the eyeglass-based tactile response device.

FIG. 6 is flowchart describing how a sensitivity level may be set by a user which allows the user to determine the level of adjustment and tactile feedback desired when directing the head direction. The process begins in step S101, wherein a user inputs a length of the forehead L, which may also correspond with the length of the track 104. Moreover, if the user chooses not to input a user specific length L through a processor interface, a preset value for L may be set by a manufacturer for the length of the track 104. The process then moves to step S102 wherein based on the length of the forehead L, the computation of movement in one degree increments (X) is made by the formula:

$$X = \frac{L}{180}. \quad (4)$$

As will be discussed below, the movement amounts may be adjusted according to a predefined table of values that corresponds with the linear movement and the degree of bearing angle change.

Figure 8:
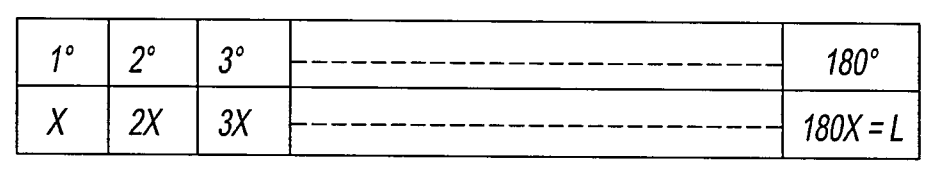

The process then proceeds to step S103 where a sensitivity level S is optionally set by the user through the processor interface. The process then proceeds to S104 where a query is made regarding whether S is set to zero. If the response to the query in step S104 is affirmative, the process proceeds to step S105 where the number of set positions (N) equals 180, which corresponds to half of a circular motion of the user's head (full turn to the left, as compared to full turn to the right). The process then proceeds to step S106, where a table (as shown in FIG. 8), of values associating the number of steps is set in a non-transitory storage medium. The process then ends.

However, if the response to the query in step S104 is negative, the process proceeds to step S107 where for S>0, a different number N is computed:

$$N = \frac{180}{S}. \quad (5)$$

Based on a different value of N as calculated by equation (5), a Table II-A (shown below) is computed in step S108, which sets a lesser number of candidate steps. Note that the sensitivity S, set by a particular user corresponds to a degree value, for example S=2·5°, 7·5° etc that signifies an acceptable region with reference to the sound source that the user has to orient his/her head position. For a user defined forehead length L=3·0 inches we depict two sample tables compared in step S108 for values of sensitivity S=10° and S=7·5° respectively.

| SAMPLE TABLE II-A: L = 3 inches, S = 10° | | |
|---|---|---|
| N | Movement | Degree |
| 0 | 0 | 0 |
| 1 | 0.1667 | 10 |
| 2 | 0.3334 | 20 |
| 3 | 0.5001 | 30 |
| 4 | 0.6668 | 40 |
| 5 | 0.8335 | 50 |
| 6 | 1.0002 | 60 |
| 7 | 1.1669 | 70 |
| 8 | 1.3336 | 80 |
| 9 | 1.5003 | 90 |
| 10 | 1.667 | 100 |
| 11 | 1.8337 | 110 |
| 12 | 2.004 | 120 |
| 13 | 2.1671 | 130 |
| 14 | 2.338 | 140 |
| 15 | 2.5005 | 150 |
| 16 | 2.6672 | 160 |
| 17 | 2.8339 | 170 |
| 18 | 3 | 180 |

| SAMPLE TABLE II-B: L = 3 inches, S = 7·5° | | |
|---|---|---|
| N | Movement | Degree |
| 0 | 0 | 0 |
| 1 | 0.125775 | 7.5 |
| 2 | 0.25155 | 15 |
| 3 | 0.377325 | 22.5 |
| 4 | 0.5031 | 30 |
| 5 | 0.628875 | 37.5 |
| 6 | 0.75465 | 45 |
| 7 | 0.880425 | 52.5 |
| 8 | 1.0062 | 60 |
| 9 | 1.131975 | 67.5 |
| 10 | 1.25775 | 75 |
| 11 | 1.383525 | 82.5 |
| 12 | 1.5093 | 90 |
| 13 | 1.635075 | 97.5 |
| 14 | 1.76085 | 105 |
| 15 | 1.88625 | 112.5 |
| 16 | 2.0124 | 120 |
| 17 | 2.138175 | 127.5 |
| 18 | 2.26395 | 135 |
| 19 | 2.389725 | 142.5 |
| 20 | 2.5155 | 150 |
| 21 | 2.641275 | 157.5 |
| 22 | 2.76705 | 165 |
| 23 | 2.892825 | 172.5 |
| 24 | 3 | 180 |

From the sample tables depicted above, it can be seen that the lower the value of sensitivity set by the user, the higher the number of sample points. For example S=7·5° results in N=24 sample points as compared to N=18 sample points obtained for S=10°.

In Table II-A and Table II-B, a correlation is made between the step number, the amount of movement (linear movement along the track 104), and the associated bearing angle degree, with a lower sensitivity value implying a more precise eyeglass based tactile response device.

Figure 7:
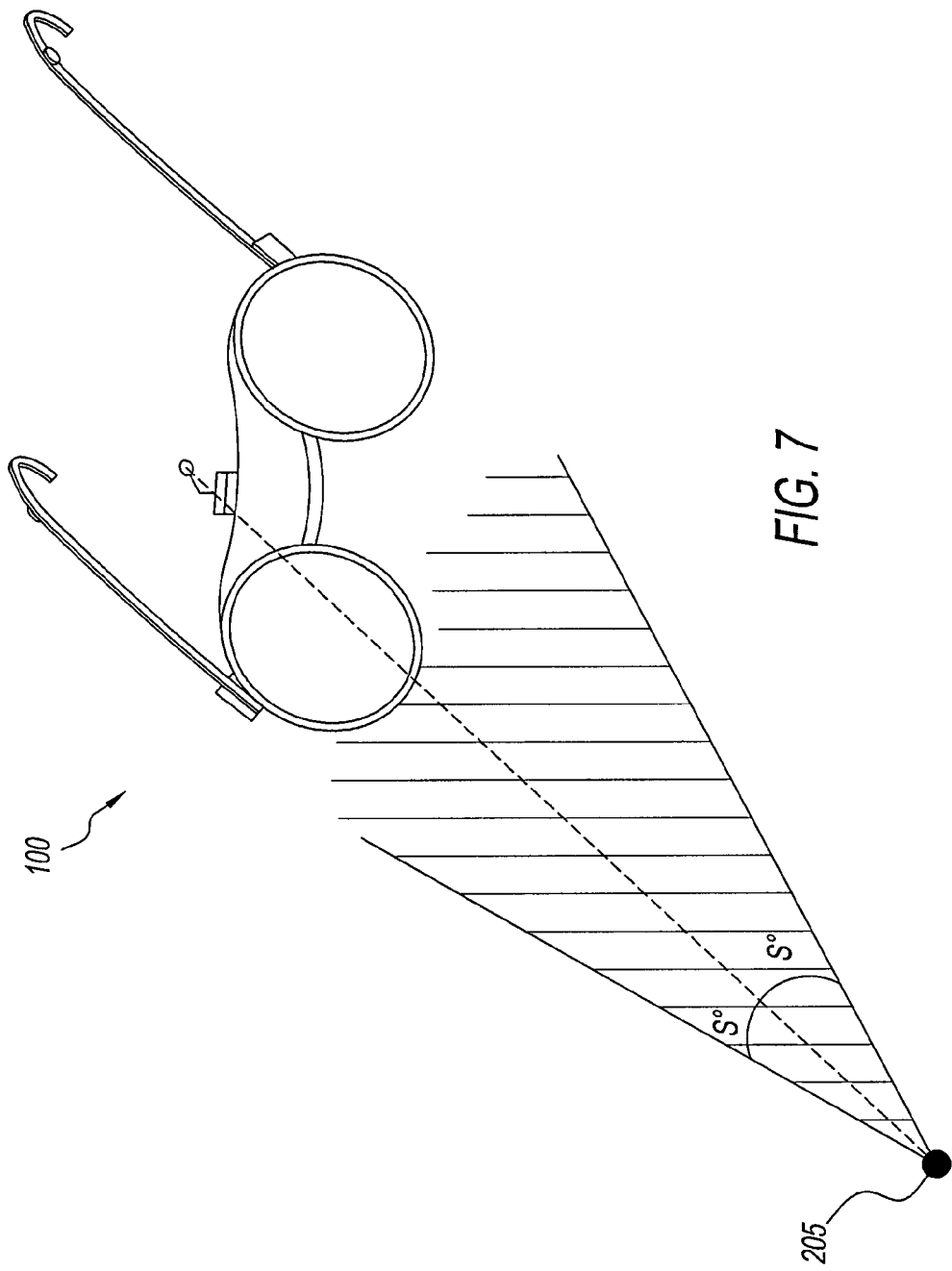
FIG. 7 is a diagram of an exemplary scenario in which the eyeglass-based tactile response device is aligned within a predetermined amount relative to a sound source.

FIG. 7 is a diagram that shows a scenario where the eyeglass-based tactile device 100 can be potentially positioned within a predetermined bearing angle 2S degrees relative to the audio source 205. Specifically, when the device 100 positions its line of sight 106, within ±S degrees relative to the audio source 205, no further tactile response is provided to the user so that the user is not constantly annoyed by the device 100 touching the user.

Figure 9:
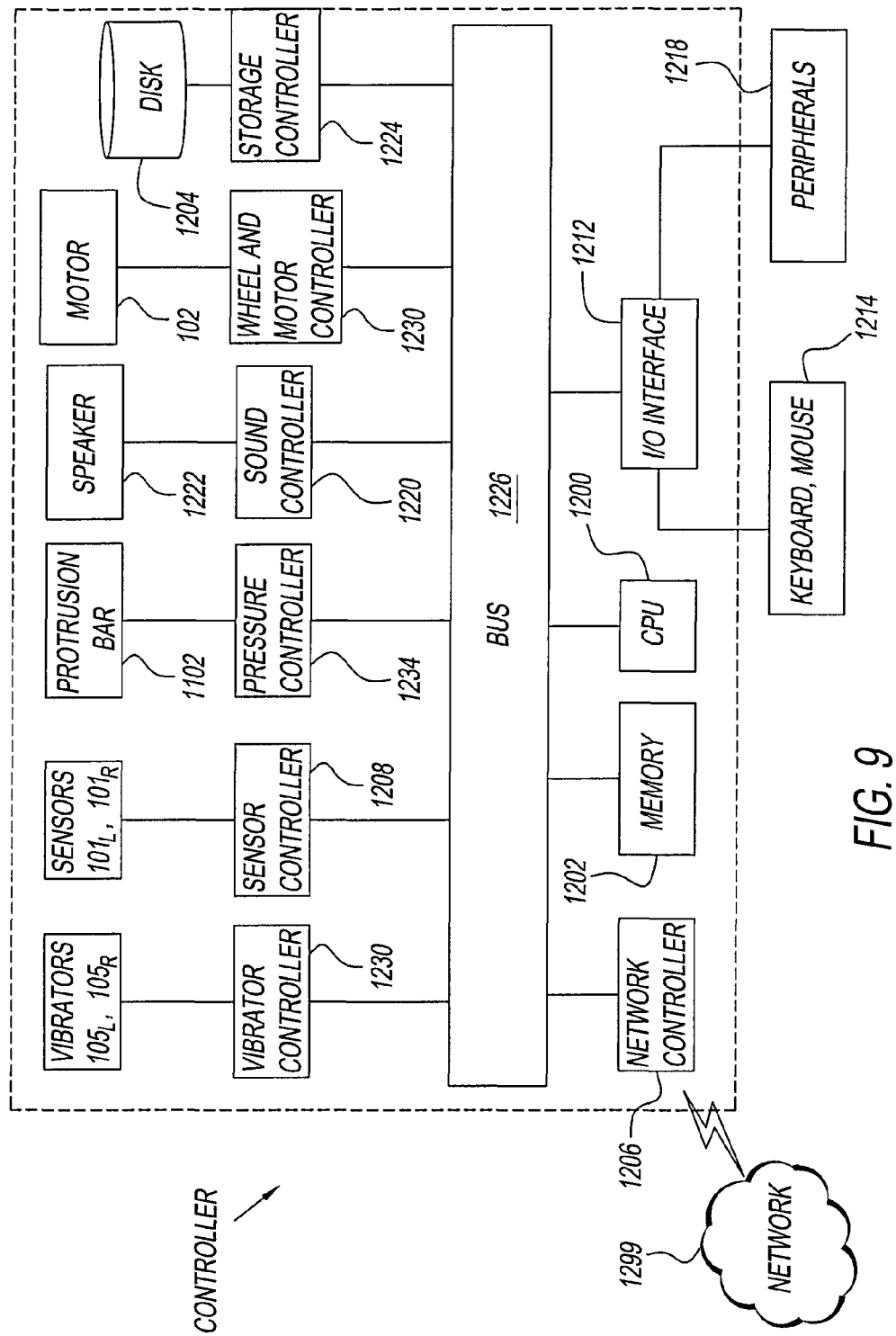
FIG. 9 is an exemplary computer processor based device that may be used either directly, or remotely, to assist in the processing of different processes employed by the eyeglass-based tactile response device.

FIG. 9 is a block diagram of a controller which may be used to perform the above-described processes. A hardware description of the controller according to exemplary embodiments is described with reference to FIG. 9. In FIG. 9, the controller includes CPU 1200 which performs the process described above. The processed data and instructions may be stored in memory 1202. These processes and instructions may also be stored on a storage medium disk 1204 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the eyeglass-based tactile response device 100 communicates, such as a server or computer.

Further, the claimed advancements may be provided as a utility application, background daemon, or component of an operating system, or combination thereof, executing in conjunction with CPU 1200 and an operating system such as Microsoft Windows 7, UNIX, Solaris, LINUX, Apple MAC-OS and other systems known to those skilled in the art.

CPU 1200 may be a Xenon or Core processor from Intel of America or an Opteron processor from AMD of America, or may be other processor types that would be recognized by one of ordinary skill in the art. Alternatively, the CPU 1200 may be implemented on an FPGA, ASIC, PLD or using discrete logic circuits, as one of ordinary skill in the art would recognize. Further, CPU 1200 may be implemented as multiple processors cooperatively working in parallel to perform the instructions of the inventive processes described above.

The controller in FIG. 9 also includes a network controller 1206, such as an Intel Ethernet PRO network interface card from Intel Corporation of America, for interfacing with network 1299. As can be appreciated, the network 1299 can be a public network, such as the Internet, or a private network such as an LAN or WAN network, or any combination thereof and can also include PSTN or ISDN sub-networks. The network 1299 can also be wired, such as an Ethernet network, or can be wireless such as a cellular network including EDGE, 3G and 4G wireless cellular systems. The wireless network can also be WiFi, Bluetooth, or any other wireless form of communication that is known.

A general purpose I/O interface 1212 interfaces with a keyboard and/or mouse 1214 as well as to a variety of peripherals 1218 including printers and scanners, such as an OfficeJet or DeskJet from Hewlett Packard. The keyboard 1214 may be a Braille keyboard, thus enabling the user to manually input the sensitivity and forehead length parameters.

A sound controller 1220 is also provided in the controller, such as Sound Blaster X-Fi Titanium from Creative, to interface with speakers/microphone 1222 thereby providing sounds and/or music. The speakers/microphone 1222 can also be used to accept dictated words as commands for controlling the controller or for providing location and/or property information with respect to the target property. The speakers/microphone 1222 may be used in the process of providing instruction, as to the sensitivity and forehead length parameters.

The general purpose storage controller 1224 connects the storage medium disk 1204 with communication bus 1226, which may be an ISA, EISA, VESA, PCI, or similar, for interconnecting all of the components of the eyeglass-based tactile response device 100.

Further, a wheel and motor controller 1230 is also provided to interface with the motor 102. The controller, will reposition (i.e., reset) the wheel to the center of the users forehead on receiving instructions of reset from CPU 1200. A sensor controller 1208 is provided to interface with the microphone based sensors $101_L$ and $101_R$. The sensor controller 1208 can be used to control the voice capturing sensitivity of the sensors which enable the user to detect different types of voice signals.

A vibrator controller 1230 is provided to adjust the vibration frequency of the vibrating device $105_L$ and $105_R$. For the alternate embodiment of the eyeglass based tactile device, a pressure controller 1234, is provided to interface with the tactile protrusion bar 1102, in order to control the amount of pressure applied by the protrusion bar.

A description of the general features and functionality of the keyboard and/or mouse 1214, as well as the storage controller 1224, network controller 1206, sound controller 1220, and general purpose I/O interface 1212 is omitted herein for brevity as these features are known.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. An eyeglass-based tactile response device comprising:
an eyeglass frame having a left frame temple and a right frame temple configured to hold the eyeglass-based tactile response device to a head of a user;
a track that interconnects a left eyepiece to a right eyepiece, said left eyepiece connected to said left frame temple, and said right eyepiece connected to said right frame temple;
a first sensor mounted on the left frame temple;
a second sensor mounted on the right frame temple;
a first haptic device disposed on the left frame temple;
a second haptic device disposed on the right frame temple; and
a drivable tactile device that includes
a motor,
a contact piece disposed on the motor,
the first sensor and the second sensor configured to detect a sound signal from a remote source, and
a controller that generates a drive signal to control the drivable tactile device to provide a tactile response and orientation guidance to the user so as to align the eyeglass-based tactile response device with the remote source.

2. The eyeglass-based tactile response device according to claim 1, wherein at least one of said left sensor is mounted to a hinge on the left frame temple and said right sensor is mounted to a hinge on the right frame temple.

3. The eyeglass-based tactile response device according to claim 1, wherein said haptic device is a vibration device.

4. The eyeglass-based tactile response device according to claim 1, wherein said contact piece is a wheel.

5. The eyeglass-based tactile response device according to claim 1, wherein said controller is configured to provide feedback until said head of the user is aligned with said remote source.

6. The eyeglass-based tactile response device according to claim 5, wherein said feedback updates direction of sound computation in response to a movement overshoot by the user.

7. A method of providing a tactile response comprising:
computing, with a processing circuit, a sensitivity table based on a predetermined sensitivity level and a forehead length of a user;
detecting a voice signal by a pair of sensors located on opposite temples of a eyeglass-based tactile response device;
processing with said processing circuit said voice signal to compute a bearing angle relative to a source of said voice signal;
driving a wheel along the forehead with a motor to provide a tactile indication to the user regarding an amount by which the user must turn the forehead to reduce a magnitude of the bearing angle; and
triggering a pair of vibration devices mounted to the eyeglass-based tactile response device.

8. The method of providing a tactile response according to claim 7, wherein said bearing angle is a magnitude of radial shift said user has to move to be aligned with said remote voice signal.

9. The method of providing a tactile response according to claim 7, wherein said predetermined sensitivity level is a predetermined angular amount with respect to said source within which said user has to be positioned to avoid another triggering.

10. The method of providing a tactile response according to claim 7, further comprising:
computing, with a processing circuit, said sensitivity table which includes a number of set positions based on said sensitivity level.

11. A non-transitory computer readable medium having stored thereon a program that when executed by a computer causes the computer to execute the steps of:
computing a sensitivity table based on a predetermined sensitivity level and a forehead length of a user;
detecting a voice signal by a pair of sensors located on opposite temples of a eyeglass-based tactile response device;
processing said voice signal to compute a bearing angle relative to a source of said voice signal;
driving a wheel along the forehead with a motor to provide a tactile indication to the user regarding an amount by which the user must turn the forehead to reduce a magnitude of the bearing angle; and
triggering a pair of vibration devices mounted to the eyeglass-based tactile response device.

* * * * *